United States Patent [19]

Payne et al.

[11] Patent Number: 4,874,696

[45] Date of Patent: Oct. 17, 1989

[54] NOVEL BACTERIUM INDUCIBLE TO PRODUCE UNIQUE STEROID-TRANSFORMING ENZYMES: PREPARATION AND APPLICATIONS THEREOF

[75] Inventors: Donna W. Payne, Columbia; Paul Talalay, Baltimore, both of Md.

[73] Assignee: The Johns Hopkins University, Med School, Baltimore, Md.

[21] Appl. No.: 790,447

[22] Filed: Oct. 23, 1985

[51] Int. Cl.$^4$ .................... C12Q 1/32; C12N 9/04; C12R 1/05

[52] U.S. Cl. .................... 435/26; 435/190; 435/252.1; 435/829

[58] Field of Search .................... 435/26, 68, 25, 829, 435/170, 29, 190, 252.1, 810

[56] References Cited

U.S. PATENT DOCUMENTS 3,777,816 12/1973 Terada et al. .
4,101,378 7/1978 Nishikawa et al. .
4,446,231 5/1984 Self .................................... 435/26 X
4,490,464 12/1984 Gorton et al. ................... 435/817 X
4,520,102 5/1985 Bunno et al. ......................... 435/829

OTHER PUBLICATIONS

Anderson, "Analogs of Pyridine Nucleotide Coenzymes", In: The Pyridine Nucleotide Coernzymes, Everse et al. (ed.), Academic Press, N.Y., 1982, pp. 91–133.
Payne et al., J. Biol. Chem. 257:663–642 (1982).
Blaedel et al., 1978, Analytical Chemistry, vol. 50, No. 8, pp. 1026–1032.
Yamaguchi et al. (1981), Analytical Letters, vol. 14, No. B6, pp. 433–438.
Hurlock et al., (1956), Society of Experimental Biology and Medical Proceedings, vol. 93, pp. 566–564.

*Primary Examiner*—Robert J. Warden
*Assistant Examiner*—Randall E. Deck

*Attorney, Agent, or Firm*—Mishrilal Jain, P.A. Holman & Stern

[57] ABSTRACT

The present invention discloses a unique biologically pure culture of a microorganism belonging to *Alcaligenes* species. The microorganism has the property of producing novel 17β-hydroxysteroid dehydrogenase (17β-HSD) capable of enzymatic reaction with an androgen and an estrogen. The methods of isolation the microorganism and the 17β-HSD have been described. An assay and a kit for detecting the presence of $C_{18}$ and $C_{19}$ steroids in biological samples have also been disclosed.

16 Claims, 5 Drawing Sheets

NOVEL BACTERIUM INDUCIBLE TO PRODUCE UNIQUE STEROID-TRANSFORMING ENZYMES: PREPARATION AND APPLICATIONS THEREOF

The invention described herein was made in the course of work under a grant from the Department of Health and Human Services, Government of the United States of America.

BACKGROUND OF THE INVENTION

1. Technical Field

The present invention is related to obtaining a novel bacterium belonging to the genus Alcaligenes and capable of producing a unique 17β-hydroxysteroid dehydrogenase as well as other steroid-transforming enzymes, to the use of these enzymes for preparative and analytical purposes, and to the description of a novel enzyme cycling assay capable of detecting picomole quantities of compounds with hydroxyl or carbonyl groups. More particularly, the present invention is directed to the isolation of a morphologically distinct bacterium belonging to Alcaligenes genus capable of being induced to produce steroid-transforming enzymes one of which, a 17β-hydroxysteroid dehydrogenase, has unexpected and unique properties. Because of their unique specificity, these enzymes can be used in the preparative transformation of certain substrates to products and for the analytical detection of steroids and other steroid-transforming enzymes.

The invention also describes a general assay for the detection of compounds with hydroxyl or carbonyl groups via the use of dehydrogenases which have specificity for two or more nicotinamide nucleotides or their analogs. A particular assay for the detection of 17β-hydroxyl- and/or 17-ketosteroids employing 17β-hydroxysteroid dehydrogenase from Alcaligenes (supra) is also described.

2. State of the Art

There are several enzymes which can be grouped under the class of hydroxysteroid dehydrogenase (HSD), such as 3α-, 3β-, 17β-hydroxysteroid dehydrogenases and the like. Certain HSDs from microbial as well as mammalian sources have been isolated. However, enzymes possessing the properties and specificities as described for the 17β-HSD of the present invention have not heretofore been known. Such unique properties of the 17β-HSD of the present invention were neither predictable nor foreseeable from the prior art. Specifically, prior to the present invention, no highly active 17β-HSD was known which is substantially free of 3β-HSD activity, and which catalyzes oxidation of 17β-hydroxyl and reduction of 17-keto groups of both $C_{19}$ and $C_{18}$ steroids. For instance, the bacterial 17β-HSD of Pseudomonas testosteroni contains significant 3β-HSD activity and even sustained efforts to obtain a 17β-HSD free of ancillary enzyme(s) have not been successful (Talalay, The Enzymes 2nd Ed., Vol. 7, pp. 177–202, Academic Press, NY, 1963; Schultz et al., J. Biol. Chem. 252:3775–3783, 1977). Further, the HSD of Brevibacterium sterolicum described in U.S. Pat. No. 3,776,816 catalyzes both 3β- and 17βHSD activity. In contrast, the 17β-HSD of the present invention, unlike the 3β- and 17β-HSD of either P. testosteroni or B. sterolicum, is substantially free of 3β-HSD activity and will not catalyze the oxidoreduction of 3β-hydroxy- or 3-keto- groups of steroids. Thus, it is a distinctly different enzyme. Similarly, the mammalian placental 17β-HSD (Jarabak et al., J. Biol. Chem. 237:345–357, 1962; Karavolas et al., J. Biol. Chem. 245:4948–4952, 1970) catalyzes the oxido-reduction of phenolic (estrogenic) 17β-hydroxysteroids and does not react with testosterone and other androgenic 17β-hydroxysteroids and 17-ketosteroids to any appreciable degree. In addition, pure placental 17β-HSD was found to have very low specific activity. Thus, finding an enzyme having the selectivity, specificity and high activity as disclosed herein was by no means predictable from the prior art.

The present invention is the first to obtain a 17β-HSD unexpectedly possessing unique properties such as highly selective and stereospecific oxido-reduction of both $C_{19}$ (androgenic) and $C_{18}$ (estrogenic) steroids at about equal rates. It should also be emphasized that the 17β-HSD of the present invention is inducibly obtained only from the bacteria belonging to the genus Alcaligenes and is not known to be obtainable from any other source. It should be further noted that without such induction, obtaining the enzyme(s) of the present invention in an amount suitable for the utilities disclosed herein is unlikely.

The Alcaligenes sp. also contains distinct, inducible 3β-HSD, and $\Delta^5$-3-ketosteroid isomerase, and may contain other inducible steroid-transforming enzymes. Although 3β-HSDs and ketosteroid isomerases have been described from other sources, it is both convenient and economical to isolate such enzymes from this species of Alcaligenes during the course of the same purification.

The transhydrogenase function of hydroxysteroid dehydrogenases with *dual* nicotinamide nucleotide specificity has been described whereby *catalytic* quantities of steroids promote the following reaction (Talalay & Williams-Ashman, Proc. Natl. Acad. Sci. U.S.A., 44, 15, 1958; Talalay, et al., Proc. Natl. Acad. Sci. U.S.A., 44, 862, 1958):

$$NADPH + NAD^{30} \rightleftharpoons NADP^{30} + NADH$$

Recently, Nicolas et al. (Clin. Chim. Acta., 92, 1, 1979) have employed the NAD(P)H-linked transhydrogenase function of placental 17β-HSD to detect picogram quantities of 17β-estradiol and estrone in plasma and urine. However, widespread usefulness of this method is limited by the relative difficulty of obtaining highly purified hydroxysteroid dehydrogenases with dual nucleotide specificity from animal sources and because of the low specific activities of such enzymes. Moreover, since placental 17β-HSD is virtually unable to catalyze the oxido-reductions of $C_{19}$ steroids, this assay cannot be used to measure testosterone and related steroids. Furthermore, such prior assay is not applicable with the many bacterial hydroxysteroid dehydrogenases which react with NAD(H) but not NADP(H), as is the case with the HSD of the present invention.

The 17β-HSD (from Alcaligenes) of the present invention has specificity for both $C_{18}$ (estrogenic) and $C_{19}$ (androgenic) steroids. Since this enzyme reacts with NAD but *not* NADP, a unique assay was developed for these steroids based on the transhydrogenase function of this enzyme which readily promotes hydrogen transfer between NAD and certain NAD-analogs. The transhydrogenase reaction of bacterial hydroxysteroid dehydrogenases with NADH and NAD-analogs was described earlier (P. Talalay, H. G. Williams-Ashman, Recent Progress in Hormone Research, Vol. 16, pages 1–47, 1960) and the assay of the present invention, provides a unique application of the transhydrogenases function to the detection of steroids. This assay is described more fully below and is applicable not only with 17β-HSD of the present invention, but with any hydroxysteroid dehydrogenase of mammalian or bacterial origin which has specificity for NAD and its analogs. Further, the assay of this invention has general application to the detection of non-steroidal compounds with hydroxyl or carbonyl groups via the transhydrogenase function of appropriate dehydrogenases which have dual specificity for NAD and its analogs.

In short, the assay of the present invention provides a simple, inexpensive, one-step procedure, using ordinary colorimetric equipment, for the detection of compounds in biological materials (e.g. serum, urine, tissue extracts, tissue culture fluid). Because of its simplicity, the assay is, of course, adaptable to automation. It is noted that this assay is unique among steroid assays in its ability to simultaneously detect "families" of steroids, and to provide profiles of certain known and unknown steroids in biological fluids.

SUMMARY OF THE INVENTION

It is, therefore, an object of the present invention to provide an isolated and substantially pure culture of a bacterial species inducible to produce processible amounts of steroid-transforming enzymes.

It is a further object of the present invention to provide a method for purifying a 17β-HSD to homogeneity from the species of Alcaligenes described herein.

It is a still further object of the present invention to provide a method for obtaining 3β-HSD and Δ$^5$-3-ketosteroid isomerase as a by-product during the purification of 17β-HSD from Alcaligenes (supra).

It is yet another object of the present invention to provide a general one-step assay method for the detection of hydroxyl and carbonyl compounds via the transhydrogenation function of dehydrogenases with multiple specificity for nicotinamide nucleotides and their analogs.

An additional object of the present invention is to provide a specific one-step assay for the detection of 17β-hydroxyl-and 17-keto-steroids via the transhydrogenation function of 17β-HSD from the species of Alcaligenes of this invention.

Various other objects and advantages including preparative and analytical applications will become apparent as the detailed description of the invention proceeds.

BRIEF DESCRIPTION OF DRAWINGS

These and other objects, features and many of the attendant advantages of the invention will be better understood upon a reading of the following detailed description when considered in connection with the accompanying drawings wherein:

Fig. 2 shows evidence for the purity of 17β-hydroxysteroid dehydrogenase. A. SDS-polyacrylamide gel electrophoresis: Standard proteins and purified 17β-HSD were subjected to electrophoresis in gels containing sodium dodecyl sulfate (SDS) as described herein. Each lane contained 10–65 μg of protein: 1. Standard proteins (molecular weight $\times 10^{-3}$) from top to bottom are: phosphorylase B, albumin, ovalbumin, carbonic anhydrase, trypsin inhibitor, α-lactalbumin. 2. Pool A from Reactive Red-120-agarose chromatography (Table IV, Step 7); 3. Pool B following repeat Red-agarose chromatography (Table IV, Step 7). The mean molecular weight of pure monomeric 17β-HSD (Lanes 2, 3) calculated from two such experiments, is about 32,000. B. Native polyacrylamide gel electrophoresis. Pure 17β-HSD (2–7μg) was subjected to electrophoresis on native gels of 12.5% total acrylamide. Gels were stained for either 17β-HSD activity with testosterone (1) or for protein with Coomassie Blue (2);

FIG. 3 shows application of 17β-HSD (from Alcaligenes sp. of the present invention) and 3α-HSD (from Pseudomonas testosteroni TB) to the selective and sequential preparation of steroid products from substrates. The selective oxidation of the 3α- and 17βhydroxyl groups of 34 μM 5α-androstane-3α, 17β-diol by 0.019 unit of either 3α-HSD or 17β-HSD (of the present invention) was monitored in a 3ml-assay system (described under "Detailed Description of Invention"). The time of addition of enzymes is indicated by the arrows. The horizontal dashed lines indicate the predicted quantities of NADH formed when one (bottom line) or two (top line) hydroxyl groups on the steroid have been completely oxidized. At each of the four plateaus shown, the steroid products were extracted from the assay mixture with ethyl acetate and subjected to normal phase HPLC and detected by refractive index (R.I.) as described in "Detailed Description of Invention". The actual chromatograms are shown in the insets. Elution times of appropriate standard steroids are indicated as follows: A. 5α-androstane-3, 17-dione; B. dihydrotestosterone; C. androsterone; D. 5α-androstane-3α, 17β-diol;

DETAILED DESCRIPTION OF INVENTION

The above objects and advantages of the present invention are achieved by a biologically pure culture of a microorganism belonging to Alcaligenes genus having the identifying characteristics of ATCC 53265.

The term "substantially pure" as defined herein means as pure as it is humanly possible employing the present conventional techniques known to one of ordinary skill in the art. The term "substantially free or devoid of activity" means less than 1% of the activity using testosterone as a substrate.

The term "biologically pure" as defined herein means the bacterial species obtained is substantially pure phenotypically or functionally but may or may not be genetically substantially pure. In other words, an isolated substantially pure bacterial species of the present invention could possibly contain phenotypically indistinguishable mutants, reassortants or other genetic variants and the like but yet may be biologically pure so long as said culture possesses the property of being inducible to produce the HSD of desired purity and specificity as described herein.

The term "processible" amount as used herein means at least such amount as is practically possible to isolate and purify by the conventional preparative or analytical tools.

All other scientific or technical terms have the same meaning as conventionally or generally understood by one of ordinary skill in the art to which the invention belongs, unless indicated otherwise.

Although any equivalent or similar methods and materials can be employed for the practice of the invention or for the tests described herein, the preferred methods and materials are now listed infra. All publications mentioned hereunder are incorporated herein by reference.

Isolation of Alcaligenes sp

Location not being a critical factor, soil samples from various locations are incubated in shaking flasks of suitable capacity at about 30° C. in a liquid medium containing a standard mineral solution (Marcus et al, 1956, *J. Biol. Chem.* 218:661–674) and 1 mg/ml of estradiol-17β, testosterone or other suitable steroids as the sole source of added carbon. When growth is evident, subcultures are made on 2% agar plates containing the same minerals and 0.1% (wt/vol) of the steroid. Microbial colonies capable of growth on the steroid are then subcultured and isolated by serial enrichment cultures following standard bacteriological techniques. All cultures capable of growth on steroids were monitored for HSD activity. For monitoring the enzymatic activity, cell suspensions from the cultures were sonically disrupted, centrifuged and the enzymatic activity for the desired HSD assayed in the supernatant fraction. Among the microorganisms selected, one, isolated by growth in estradiol-17β as the sole source of organic carbon, was the Alcaligenes sp. of the present invention.

Enzyme Assays

The hydroxysteroid dehydrogenases were assayed spectrophotometrically at 340 nm as described by Shikita and Talalay, *Analyt. Biochem.* 95:286–292, 1979. In the direction of oxidation, the assay systems contained in a final volume of 3 ml: 100 mM 2-(cyclohexylamino-ethanesulfonic acid) (CHES), pH 9.0; 0.33 mM NAD; 0.05% bovine plasma albumin; and 34 μM of the appropriate steroid added in 30 μl of methanol. In the reductive direction, the assay systems contained in a final volume of 3 ml: 20 mM 2-(N-morpholino)ethanesulfonic acid (MES), pH 7, 0.33 mM NADH, 0.05% bovine plasma albumin, and 34 μM of the appropriate steroid added in 30 μl of methanol. Activity with androsterone indicated the presence of 3α-HSD; activity with dehydroepiandrosterone indicated the presence of 3β-HSD, and activity with estradiol-17β or testosterone indicated the presence of 17β-HSD. $\Delta^5$-3-ketosteroid isomerase was assayed according to Kawahara (*Methods Enzymol.* 5, 527–539, 1962) at 248 nm. One unit of enzyme activity is defined as the quantity required to transform 1 μmol of designated substate per min under the specified reaction conditions.

Identification of Organism

An isolated subculture of one of the microorganisms (designated M21), isolated by enrichment culture on estradiol-17β and which contained 17β-HSD, 3β-HSD, and $\Delta^5$-3-ketosteroid isomerase was sent to ATCC (American Type Culture Collection, Rockville, Md.) for morphological and biochemical characterization. The culture identification made by ATCC of the strain M21 is as follows.

Morphology:

Colonies of M21 grown on nutrient agar for 24 hours are convex, opaque, circular with entire margins, and 1 mm in diameter. After 24 hours of incubation a non-diffusible yellow pigment becomes evident; at 96 hours, the pigment is bright yellow and the colonies may be 3 mm in diameter.

At 14 days, papillae or secondary colonies form on the surface and edge of the original colonies. This is a common occurrence when plates are held for a long time. These daughter colonies appear after the first growth is mature and no longer growing. The cells in these colonies differ genetically from the parent colony. To prevent the proliferation of such mutants, the stocks of the strain should be stored in liquid nitrogen or as lyophilized cultures.

Cells are gram negative short rods and coccobacilli. They are actively mobile and possess one to eight peritrichous flagella. Cells occur singly, in pairs, and short chains. When grown in a low nitrogen medium containing DL-hydroxybutyrate, the bacterium synthesizes poly β-hydroxybutyrate and forms inclusions.

Biochemical and Physiological Characteristics:

Strain M-21 is biochemically relatively inert as demonstrated by the data shown in Tables I–III. The strain is aerobic, non-saccharolytic, and oxidase positive. Nutritionally, it is very limited, utilizing only seven of the more than 50 compounds tested as sole source of carbon and energy. (Table I–III).

TABLE I

Special Contract 603
Biochemical and Physiological Tests:

| | | |
|---|---|---|
| 4 C growth | − | 7 days |
| 25 C growth | + | 7 days |
| 30 C growth | + | 7 days |
| 37 C growth | W | 7 days |
| 41 C growth | − | 7 days |
| Fluorescein produced | − | 7 days |
| Pyocyanine produced | − | 7 days |
| Diffusible orange | − | 7 days |
| Diffusible yellow | − | 7 days |
| Diffusible purple | − | 7 days |
| Non-diffusible green | − | 7 days |
| Other non-diff. pigments | + | Yellow |
| Diffusible brown (melanin) | + | 7 days |
| pH 6.0 growth | + | 1 day |
| 3% NaCl growth | − | 7 days |
| 6.5% NaCl growth | − | 7 days |
| MacConkey agar growth | − | 7 days |
| Skim milk agar growth | − | 7 days |
| Aesculin hydrolysis | − | 7 days |
| Casein hydrolysis | − | 7 days |
| Starch hydrolysis | − | 7 days |
| Gelatinase | + | 7 days |
| Tween 20 hydrolysis | + | 2 days |
| Tween 80 hydrolysis | − | 7 days |
| Indole | − | 7 days |
| Simmons citrate growth | − | 7 days |
| Urease | − | 7 days |
| Nitrate to nitrite | − | 7 days |
| Nitrite reduction | − | 7 days |
| Nitrite to nitrogen gas | − | 7 days |
| Hydrogen sulfide (TSI) | − | 7 days |
| Lysine decarboxylase | − | 14 days |
| Arginine (Mollers) | − | 14 days |
| Ornithine decarboxylase | − | 14 days |
| Phenylalanine deamination | − | 7 days |
| Lecithinase | − | 7 days |
| Phosphatase | + | 7 days |
| Catalase | + | 2 days |
| Oxidase | + | 2 days |
| Gluconate oxidation | − | 7 days |
| Growth on malonate sole carbon source | − | 7 days |
| Tyrosine degradation | + | 7 days |
| dl-hydroxybutyrate growth | + | 7 days |
| PHB accumulation | + | 7 days |
| Deoxyribonuclease | − | 7 days |
| Growth on 0.05% cetrimide | − | 7 days |
| Growth on acetate as sole carbon source | + | 7 days |
| 10 U penicillin sensitive | − | 1 day |
| 300 mcg. polymyxin sensitive | + | 1 day |
| Testosterone degradation | W | 7 days |

W = Weakly positive

TABLE II

Special Contract 603
Single Carbon Source Utilization:

| | | |
|---|---|---|
| L-arabinose | − | 7 days |
| cellobiose | − | 7 days |
| D-fructose | − | 7 days |
| lactose | − | 7 days |
| maltose | − | 7 days |
| D-mannitol | − | 7 days |
| L-rhamnose | − | 7 days |
| D-ribose | − | 7 days |
| D-sorbitol | − | 7 days |
| sucrose | − | 7 days |
| trehalose | − | 7 days |
| D-xylose | − | 7 days |
| adonitol | − | 7 days |
| erythritol | − | 7 days |
| glycerol | − | 7 days |
| ethanol | − | 7 days |
| geraniol | − | 7 days |
| i-inositol | − | 7 days |
| sebacic acid | + | 7 days |

TABLE II-continued

Special Contract 603
Single Carbon Source Utilization:

| | | |
|---|---|---|
| acetamide | − | 7 days |
| adipate | − | 7 days |
| benzoate | − | 7 days |
| butyrate | + | 7 days |
| citraconate | − | 7 days |
| D-gluconate | − | 7 days |
| M-hydroxybenzoate | − | 7 days |
| 2-ketogluconate | − | 7 days |
| DL-lactate | − | 7 days |
| L-malate | − | 7 days |
| pelargonate | − | 7 days |
| propionate | − | 7 days |
| quinate | − | 7 days |
| succinate | − | 7 days |
| L-+-tartrate | − | 7 days |
| valerate | W | 7 days |
| B-alanine | − | 7 days |
| D-A-alanine | − | 7 days |
| betaine | − | 7 days |
| glycine | − | 7 days |
| L-histidine | W | 7 days |
| DL-norleucine | − | 7 days |
| L-proline | − | 7 days |
| D-tryptophan | − | 7 days |
| L-valine | − | 7 days |
| DL-arginine | − | 7 days |
| benzylamine | − | 7 days |
| butylamine | − | 7 days |
| putrescine | − | 7 days |
| mesoconate | − | 7 days |
| DL-glycerate | − | 7 days |
| L-tryptophan | − | 7 days |

W = weakly positive

TABLE III

Special Contract 603
Strain is inhibited by .008% Bromthymolblue.
Use O-F medium containing only .003% BTB

| O-F MEDIUM | | Days |
|---|---|---|
| Acid from L-arabinose | K | 1 day |
| Acid from cellobiose | K | 5 days |
| Acid from ethanol | K | 1 day |
| Acid from D-fructose | K | 1 day |
| Acid from D-glucose A02 | K | 1 day |
| Acid from D-glucose An02 | − | 1 day |
| Alkaline pH in D-glucose | + | 1 day |
| Acid from glycerol | + | 5 days |
| Acid from i-inositol | K | 1 day |
| Acid from lactose | K | 7 days |
| Acid from maltose | K | 7 days |
| Acid from D-mannitol | K | 5 days |
| Acid from D-mannose | − | 14 days |
| Acid from L-rhamnose | K | 5 days |
| Acid from D-ribose | − | 14 days |
| Acid from sucrose | K | 1 day |
| Acid from trehalose | K | 7 days |
| Acid from D-xylose | K | 7 days |
| Control | K | 1 day |

K indicates alkaline color change
— indicates no color change

Identification:
Based on the basic characteristics of strain M21, the drug susceptibility pattern, and the presence of poly-β-hydroxybutyrate inclusions, this strain is identified as belonging to the genus Alcaligenes. It differs from other Alcaligenes strains by its ability to hydrolyze gelatin, its inability to grow on MacConkey's agar, and its limited utilization of carbon substrates.

"Since this strain does not conform to the descriptions of named Alcaligenes species, it can be identified as an 'Alcaligenes-like' strain or as Alcaligenes sp."

A deposit of this Alcaligenes species has been made at the ATCC under accession number 53265 and shall be maintained in viable condition at the ATCC during the entire term of the issued patent and shall be available to any person or entity without restriction but consistent with the provisions of the law.

Growth of M-21 and Enzyme Induction—Small scale growth of M21 microorganisms can be carried out at about 30° C. in shaking flasks containing 1% yeast extract in a mineral solution (Marcus et al, supra). Large scale growth of Alcaligenes sp. (M21) is performed at 30° C. in a Fermatron Fermentor (New Brunswick Scientific Co., New Brunswick, NJ) containing about 150 liters of the same medium. The fermentor is inoculated with 2% (v/v) of an overnight culture of Alcaligenes sp. The culture is aerated at 80 liters/min and stirred at 100 rpm. The medium is continuously adjusted with HCl to pH 6.5-6.8 and an anti-foaming agent (Polyglycol P 2000 Dow Chemical, Midland, MI) is added as needed.

Regardless of culture size, induction of HSD synthesis is achieved as follows: Cell growth is monitored by absorbance at 650 nm. Toward the end of logarithmic growth phase (about 18 h for Alcaligenes sp.) progesterone (200 µg/ml of culture) in acetone (1% final concentration) is added to induce enzyme synthesis. Estradiol-17β also induces enzyme synthesis in this organism. Since progesterone is a relatively inexpensive steroid among effective inducers of steroid metabolizing enzymes, it is a preferred steroid among other possible steroids for induction of enzyme synthesis in Alcaligenes sp. Induction with steroid (supra) produces about 12-20 fold increase in enzyme activity. The cells are then harvested at about 24-42 h of growth. Cell suspensions from the cultures are sonically disrupted, centrifuged, and the supernatant fractions assayed for desired enzymatic activity as described supra.

Of course, it should be quite clear that the induced enzymes do not necessarily require to be isolated from the microorganism. In other words, the microorganism or any part thereof containing the induced enzymes can be used as such in the steroid transforming process without separating the enzymes from the microorganisms.

Polyacrylamide Gel Electrophoresis: Native Gels

Electrophoresis was performed at 4° C. in tube gels at pH 7.8 (system D of Rodbard and Chrambach, *Analyt. Biochem.* 40:95-134, 1970, as modified by Carlson et al., *Biochemistry* 16:4288-4296, 1977). The apparatus used was Model GT (Hoeffer Scientific, San Francisco, CA) and the voltage was kept constant at 50 volts for 30 mins. followed by setting amperage constant for 1-2 h at 2 mamp per gel. The gels consisted of a 2.5% stacking gel and a running gel of 7-14% total acrylamide. The gels were stained either for total protein with Coomassie Blue R250 (in methanol:acetic acid:water; 5:1:5) and destained (7.5% acetic acid in 5% methanol), or stained for enzymatic activity with nitroblue tetrazolium-phenazine methosulfate (Schultz et al., *J. Biol. Chem.* 252:3775-3783, 1977). The steroid substrates were dissolved in methanol. Following color development, the reaction was stopped by transferring the gels to the above destaining solution.

Sodium Dodecyl Sulfate Gels—Slab gel electrophoresis was performed at 25° C. according to Laemmli, *Nature* 227:680-685 (1970), but with the use of a 7% acrylamide stacking gel and a 17.5% acrylamide running gel. A model SE400 unit (Hoeffer Scientific) was employed and gels were electrophoresed at 15 mAmp for about 15 h. The gels were stained with Coomassie Blue R250, as described above.

Isoelectrofocusing Gels—Flat bed electrofocusig in thin layer polyacrylamide gels was performed on an LKB 2117 Multiphor system (LKB Instruments, Gaithersburg, MD) at 4° C. for 2.5 h (25 watts at constant power) in the pH range of about 4.5-7. Gels contained 4.7% acrylamide, 0.15% bis-acrylamide and 4.9% ampholines (LKB). Focusing of proteins was complete in 2 h, irrespective of the position of application of the sample in relation to the electrodes. The pH values of such gels were determined with a surface electrode, and remained stable for at least 4 h.

High Pressure Liquid Chromatography—Proteins were separated by molecular size on column (300×7.5 mm) of hydrophilic bonded-phase silica (BioSil TSK-250; Bio-Rad Rockville Centre, NY) with the use of a Waters (Milford, MA) HPLC system. Proteins were eluted at 2 ml/min at about 24° C. in 150 mM potassium phosphate buffer, pH 7, and detected by absorbance at 220 nm. Steroids were separated by chromatography on a normal phase silica column (Partisil 10, Whatman, Clifton, NJ), and were eluted with hexane: ethyl acetate (70:30) at 2 ml per min at about 24° C. The steroids were detected by the changes in refractive index.

PURIFICATION OF 17β-HYDROXYSTEROID DEHYDROGENASE

The progress of the purification procedure is summarized in Table IV. All steps were performed at 4° C. All centrifugations were at about 12,000-16,000×g for 30 min. Protein concentrations were determined according to Bradford (Anal. Biochem. 72:248-254, 1976). The 150-liter culture (vide supra) of Alcaligenes sp. yielded about 987 g of packed wet weight of cells. The cells were harvested by centrifugation in a refrigerated continuous flow centrifuge, resuspended and washed twice with 30 mM potassium phosphate and 1 mM EDTA, pH 7.0, and stored at about −20° C. (Table IV).

TABLE IV

Large-scale Purification of 17β-hydroxysteroid dehydrogenase from Alcaligenes sp.
The purification was carried out on 987 g of wet cell weight obtained from a 150-liter fermentation. Details of the purification procedure are given in the Supplement. All enzymatic assays were performed with testosterone as substrate.

| Purification step | Total protein (mg) | Total activity (units) | Specific activity (units) | Yield (%) | Purification factor (-fold) |
|---|---|---|---|---|---|
| 1. Supernatant fraction after sonic treatment | 45,195 | 19,809 | 0.44 | 100 | 1 |
| 2. Polymin P supernatant | 13,047 | 17,560 | 1.3 | 89 | 3.1 |
| 3. Dialyzed ammonium sulfate precipitate | | | | | |

TABLE IV-continued

Large-scale Purification of 17β-hydroxysteroid dehydrogenase
from Alcaligenes sp.
The purification was carried out on 987 g of wet cell weight obtained from
a 150-liter fermentation. Details of the purification procedure are given in the
Supplement. All enzymatic assays were performed with testosterone as substrate.

| Purification step | Total protein (mg) | Total activity (units) | Specific activity (units) | Yield (%) | Purification factor (-fold) |
|---|---|---|---|---|---|
| (30–78%) | 9,768 | 10,191 | 1.0 | 51 | 2.4 |
| 4. First DEAE-cellulose chromatography | 1,620 | 11,579 | 7.1 | 59 | 16 |
| 5. Second DEAE-cellulose chromatography | 588 | 9,856 | 16.8 | 50 | 38 |
| 6. Hydrophobic chromatography (Phenyl-Sepharose) | 217 | 7,990 | 36.8 | 40 | 84 |
| 7. Affinity chromatography (Red-agarose) total | 33 | 7,895 | 239 | 40 | 544 |
| Pool A | 8.9 | 2,919 | 326 | | |
| Pool B (after chromatography) | 9.4 | 3,062 | 326 | | |
| 8. Final (after concentration) | 14.5 | 4,871 | 335$^a$ | 25 | 763 |

$^a$Mean value for pools A and B.

The following solutions, all of which contained 1 mM EDTA (ethylenediaminetetraacetic acid) and 1 mM DTT (dithiothreitol), were used:

Solution A: 30 mM potassium phosphate and 20% (v/v) glycerol, pH 7.0
Solution B: 5 mM potassium phosphate, pH 7.0
Solution C: 15 mM Tris-HCl, pH 8.0 (at 4° C.)
Solution D: 15 mM Tris-HCl, 350 mM NaCl, pH 8.0 (at 4° C.)
Solution E: 20 mM potassium phosphate, pH 7.5

Step 1: Sonification—The washed cells were thawed, suspended in 3.3 liters of Solution A and sonically disrupted in batches in a cooled, jacketed vessel with a Model 200 Sonifier (Branson Sonic Power Co., Danbury, CT) for 1 h at the highest setting for each 250 ml of suspension. Temperature was carefully maintained at about 4° C. by continuous cooling of the vessel. It was discovered from preliminary studies that the presence of 20% glycerol in the sonification buffer was necessary to prevent the loss of enzyme activity. The sonicated cells may be stored at −20° C. for many months without major loss of activity. The thawed cells were centrifuged and the sediment was washed with Solution A and re-centrifuged. The combined supernatant fluids contained 45.2 g of protein and 19,800 units of activity when measured with testosterone (i.e. 17β HSD) and 10,600 units of activity when measured with dehydroepiandrosterone (i.e. 3β-HSD) and 500,000 units activity when measured with Δ$^5$-androstene-3,17-dione (i.e., Δ$^5$,3-ketosteroid isomerase).

Step 2: Precipitation of nucleic acids—An aqueous solution of 10% (v/v) polyethyleneimine (adjusted to pH 7.0) (Polymin P, Bethesda Research Laboratories, Bethesda, MD) was added rapidly to the supernatant fluid from Step 1 to a final concentration of 0.5% Polymin P (v/v). The mixture was centrifuged, the pellet was washed with Solution A, and recentrifuged. This highly efficient procedure for precipitating nucleic acids (Rhodes et al., *J. Biol. Chem.* 254:7465–7467, 1979) also removed 71% of the total protein with little loss of enzyme activity.

Step 3: Ammonium sulfate fractionation—The pH was adjusted to about 7.0 with ammonium hydroxide during this procedure. Ammonium sulfate (168 g/liter) was added to achieve 30% saturation, the suspension was centrifuged and the pellet was discarded. Ammonium sulfate (314 g/per liter) was then added to achieve 78% saturation and the suspension was stirred slowly overnight. The centrifuged 30–78% ammonium sulfate precipitate was dissolved in 250 ml of Solution B and dialyzed overnight against the same medium. It should be understood of course, that the overnight procedures are performed as a matter of convenience only and suitable adjustment to such steps can be easily made by one of ordinary skill in the art.

Step 4: First DEAE-cellulose chromatography. The dialyzed preparation was applied to a DEAE-cellulose column (about 58.5×5 cm) equilibrated with solution B. Protein was eluted with a 4-liter linear gradient of 5 to 300 mM potassium phosphate at pH 7.0 at a rate of 5.6 ml/min. 17β-HSD activity emerged at approximately 140–180 mM potassium phosphate in yellow-colored fractions immediately preceding a band of dark red material and was purified further as described below. 3β-HSD activity was eluted in the red fractions (170–210 mM potassium phosphate). Significant quantities (4400 units) of semi-pure (1.2 unit/mg protein) 3β-HSD were contained in these side fractions. Most of the protein was retained by the column. Fractions containing 91% of the 17β-HSD activity applied to the column were pooled, precipitated with ammonium sulfate (0–80% of saturation), and dialyzed against Solution C.

Step 5: Second DEAE-cellulose chromatography—The dialyzed enzyme was applied to a DEAE-cellulose column (44.5×2.9 cm) equilibrated with Solution C. Protein was eluted with a 400-ml linear gradient of 0 to 350 mM sodium chloride in Solution C at a rate of 2.1 ml/min. 17β-HSD activity emerged at approximately 225–300 mM sodium chloride in red-colored fractions. The fractions, containing 85% of the activity applied to the column, were pooled, and additional sodium chloride was added to a final concentration of about 350 mM.

Step 6: Phenyl-Sepharose chromatography—The pooled fractions, containing a high concentration of salt (Step 5), were applied directly to a Phenyl-Sepharose column (about 15.5×2.5 cm) equilibrated with Solution D. Protein was eluted with the same buffer at 1.6 ml/min. 17β-HSD activity emerged in the clear, unretained protein fraction; the red-colored proteins were retained on the column. Fractions containing 92% of the activity applied to the column were pooled, precipitated with ammonium sulfate (0–65% of saturation) and dialyzed against solution E.

Step 7: Affinity chromatography—The dialyzed enzyme was applied to a Reactive Red 120-agarose column (about 27.5×2 cm) equilibrated with Solution E. Protein was eluted with a 285-ml linear gradient from 0 to 1 M potassium chloride and 0 to 30% (v/v) glycerol (0.71 ml/min) in Solution E. As mentioned before, a stabilizing agent such as glycerol, is preferable to preserve the enzyme activity for long term storage, for more than one year. 17β-HSD activity (98%) emerged at approximately 0.45–0.7 M potassium chloride and 13–21% glycerol. Enzyme activity was coincident with an isolated protein peak. The leading half of this peak was pooled (Pool A) and concentrated (Step 8). It contained about 2919 units of 17β-HSD activity and 8.9 mg of protein, at a specific activity of about 326 units/mg for testosterone. The trailing half of the enzyme peak (Pool B; spec. act. 250 umol/min/mg) was dialyzed overnight against Solution E and rechromatographed on the same column, and under the same conditions except that glycerol was omitted from the elution buffer. 17β-HSD activity (88%) emerged at approximately 0.75–0.85 M potassium chloride, coincident with an isolated protein peak. The major portion of this peak, containing about 3062 units of activity and 9.4 mg of protein (spec. act. about 326 units/mg), was pooled and concentrated.

Step 8: Concentration—The pure 17β-HSD preparations were simultaneously dialyzed and concentrated under a vacuum (Micro-Pro-Di-Con, Model 320, BioMolecular Dynamics, Beaverton, OR) against a solution containing 20 mM potassium phosphate, 50% glycerol, 1 mM DTT, 1 mM EDTA, pH 7.5, and stored at −20° C. The total final activity of 17β-HSD in the combined Pools A and B was about 4871 units (measured with testosterone) in a volume of 12 ml (14.5 mg protein). The substrate specificity and kinetic constants of purified 17β-HSD are shown in Tables V and VI, respectively. Compounds No. 20 to 28 (Table V) are all 3β-hydroxysteroids. As indicated, 17β-HSD of the present invention is substantially devoid of activity with these substrates.

TABLE V

Steroid substrate specificity of purified 17β-hydroxysteroid dehydrogenase of Alcaligenes sp.

The initial velocities of oxidation were measured in the standard enzyme assay system (0.33 mM NAD, 34 μM steroid, pH 9.0) with 5.7 ng of purified 17β-hydroxysteroid dehydrogenase. The velocities were normalized to a value of 100 for the oxidation of testosterone (specific activity, 326 units/mg of protein). The substrate concentrations were selected to be about 10 times the $K_m$ for testosterone (3.6 μM). For substrates showing less than 2% of the oxidation velocity of testosterone, 50–150 times more emzyme was used. All values are the means of two to three determinations.

| Compound No. | Substrate | Relative velocity |
|---|---|---|
| 1 | 17β-Hydroxy-4-androsten-3-one (testosterone) | 100 |
| 2 | 6β,17β-Dihydroxy-4-androsten-3-one | 84 |
| 3 | 11α,17β-Dihydroxy-4-androsten-3-one | 156 |
| 4 | 11β,17β-Dihydroxy-4-androsten-3-one | 136 |
| 5 | 15α,17β-Dihydroxy-4-androsten-3-one | 131 |
| 6 | 4-Androstene-3β,17β-diol | 75 |
| 7 | 5-Androstene-3β,17β-diol | 33 |
| 8 | 17β-Hydroxy-5α-androstan-3-one(dihydrotestosterone) | 133 |
| 9 | 17β-Hydroxy-5β-androstsan-3-one | 86 |
| 10 | 5α-Androstane-3β,17β-diol | 72 |
| 11 | 5α-Androstane-3α,17β-diol | 85 |
| 12 | 5β-Androstane-3α,17β-diol | 57 |
| 13 | 1,3,5(10)-Estratriene-3,17β-diol (estradiol-17β) | 72 |
| 14 | 1,3,5(10)-Estratriene-3,16α,17β-triol (estriol) | a |
| 15 | 1,3,5(10)-Estratriene-3,16β,17β-triol | 1 |
| 16 | 1,3,5(10)-Estratriene-3,16β-diol | 1.1 |
| 17 | 17α-Hydroxy-4-androsten-3-one (epitestosterone) | a |
| 18 | 1,3,5(10)-Estratriene-3,17α-diol | a |
| 19 | 11β,17α,21-Trihydroxy-4-pregnene-3,20-dione (cortisol) | a |
| 20 | 3β,17α-Dihydroxy-5-pregnene-20-one (17α-hydroxypregnenolone) | a |
| 21 | 3β-Hydroxy-5-androsten-17-one (dehydropiandrosterone) | a |
| 22 | 3β-Hydroxy-5-chloenic acid | a |
| 23 | 3β-Hydroxy-5β-androstan-17-one | a |
| 24 | 3β-Hydroxy-5β-pregnan-20-one | a |
| 25 | 3β-Hydroxy-5β-cholanic acid | a |
| 26 | 3β-Hydroxy-5α-cholanic acid | 0.2 |
| 27 | 5α-Androstane-3β,17α-diol | 0.8 |
| 28 | 3β-Hydroxy-5α-androstan-17-one (epiandrosterone) | 0.9 |
| 29 | 3α-Hydroxy-5α-androstan-17-one (androsterone) | a |

[a]Assay detection limit; equivalent <0.3% of testosterone.

TABLE VI

Kinetic constants for purified 17β-hydroxysteroid dehydrogenase Enzymatic activity was assayed as described under "Experimental Procedures". Assays were performed at pH 9 with 5.7 ng of pure 17β-HSD except for the reduction of 4-androstene-3,17-dione (pH 7; 113 ng 17β-HSD). Values for $K_m$ and $V_{max}$ were calculated from a double reciprocal plot of 7–11 assay points by use of a weighted linear regression analysis (Wilkinson, Biochem. J., 80, 324–332, 1961).

| Substrate[a] | Cosubstrate[b] | $K_m$ (μM) | $V_{max}$ (μmol/min/mg) |
|---|---|---|---|
| Testosterone | NAD | 3.6 ± 0.5[c] | 303 ± 14 |
| | S-NAD | 9.9 ± 2.2 | 224 ± 24 |
| | NADP | no activity | |
| Estradoil-17β | NAD | 6.4 ± 1.1 | 356 ± 27 |
| | S-NAD | 13.9 ± 2.2 | 136 ± 12 |
| | NADP | no activity | |
| 4-Androstene-3,17-dione | NAOH | 1.6 ± 0.3 | 17.6 ± 0.6 |
| NAD | Testosterone | 27 ± 3.5 | 333 ± 12.5 |

[a]Substrate concentrations were varied (1.6–30 μM for steroids; 10–830 μM for NAD).
[b]Cosubstrate kept constant (330 μM for nicotinamide nucleotides; 34 μM for testosterone).
[c]Means ± S.E.

Estimation of apparent moleculer weight of purified 17β-hydroxysteroid dehydrogenase by gel filtration Gel permeation HPLC of 4 μg of purified, native, dimeric, 17β-HSD was carried out on a hydrophilic silica column in 150 mM potassium phosphate, pH 7 following standard procedure. The absorption peaks (220 nm) define the elution volume ($V_e$). The void volume ($V_O$) was determined with Blue Dextran. Similarly, 4 μg of each standard protein (such as bovine serum albumin, myoglobin, IgG) was chromatographed, and a linear plot of log molecular weight with respect to $V_e/V_O$ was constructed following standard procedure. Each point on the standard curve was the mean of 1–3 determinations. The unweighted linear regression line obeyed the relation: $M_r = 7 - 1.36 \times (V_e/V_O)$. The calculated molecular weight for 17β-HSD from this regression is 68,000±6,100 (n=5).

Estimation of the apparent molecular weight of purified 17β-hydroxysteroid dehydrogenase by Ferguson analysis Polyacrylamide gel electrophoresis of purified 17β-HSD and of standard proteins were performed on gels of varying concentration and Ferguson plots (Ferguson, 1964 Metabolism 13:985–1002) were constructed by a weighted linear regression of log $R_F$ with respect to gel concentration (%) and the slope $(K_R)\pm$S.D. for each line was determined (correlation coefficients, r=0.96–0.99). The line was established by unweighted linear regression (correlation coefficient, r=0.99). The calculated $\bar{R}$-value for native, dimeric 17β-HSD was 2.92±0.1 nm and the estimated molecular weight was found to be 86,000±9,500.

The substantially pure nature of 17β-HSD obtained and its capacity to catalyze the reaction of androgen and estrogen clearly demonstrate the unique nature of the isolated Alcaligenes microorganism and the 17β-HSD obtained therefrom. Tables VII and VIII list the distinctive differences of the 17β-HSD of the present invention compared to other similarly named enzymes. The data presented in Table VII and VIII clearly demonstrate the unexpected nature of the properties found in the newly discovered 17β-HSD.

TABLE VII

| | Differences Between Two 17β-Hydroxysteroid Dehydrogenases | |
|---|---|---|
| | Source | |
| Characteristics | Alcaligenes (Bacterial)[1] | Placenta (Human) |
| Specifity for NADP(H) | no | yes[2,3,4] |
| Specificity for 17β-hydroxy-steroids with a non-aromatic A Ring | yes | no[3,4] |
| $K_m$ (μM) for 17β-estradiol with NAD | 6.4 | 14[4] |
| $V_{max}$ (μmol/min/mg protein) for 17β-estradiol with NAD | 356 | 12[4] |
| Unstable at 2 to 5 °C. | no | yes[2,3] |
| Number of bands on isoelectric-focusing | one | multiple[3] |

[1]Payne & Talalay, J. Biol. Chem., in press, 1985
[2]Talalay, On Cancer and Hormones, Univ. Chicago, p. 271–289, 1962
[3]Engel & Groman, Rec. Prog. Horm. Res., 30, 139–169, 1974
[4]Karavolas, et al., J. Biol. Chem., 245, 4948–4952, 1970

Preparative Applications of Hydroxysteroid Dehydrogenases

Because steroids may have many functional groups, the carrying out of oxidations or reductions at selective points and with known stereospecificity on the steroid skeleton and side chain, presents unusual difficulties. The 17β-hydroxysteroid dehydrogenase of the present invention has been found to effect such selective oxidoreductions in either direction with great facility, e.g.,

4-Androstene-3,17-dione + NADH +

Of course, these reactions can be made quantitative in either direction, by defining the reaction conditions well within the knowledge of one of ordinary skill in this art.

If both 3β-HSD and 17β-HSD are utilized, either simultaneously or sequentially, positionally specific and stereospecific oxido-reductions at two positions of the steroid skeleton can be obtained, e.g.:

5α-androstane-3,17-dione + 2 NADH +

2 NAD+

Figure 1:
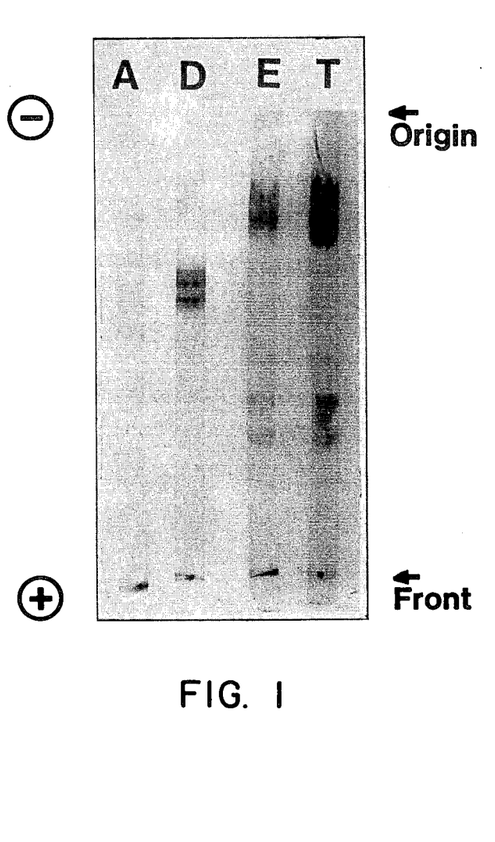
FIG. 1 shows polyacrylamide gel electrophoresis of hydroxysteroid dehydrogenase activities in sonic extracts from the Alcaligenes sp. Crude sonicates of progesterone-induced Alcaligenes sp. cultures were prepared, subjected to electrophoresis on 12.5% native polyacrylamide gels, and stained for activity using various steroids as substrates. Each gel contained 175 μg of total protein and at least 0.038 unit of HSD activity. Activity stains contained (as substrates): androsterone (A), (indicating lack of 3αHSD); dehydroepiandrosterone (D), (indicating 3βHSD; isoenzymes separable from 17β-HSD isoenzymes); estradiol-17β (E) or testosterone (T), (the latter two substrates indicate the presence of 17β-HSD isoenzymes with specificity for both estrogens and androgens; and separable from 3β-HSD)
Figure 2:
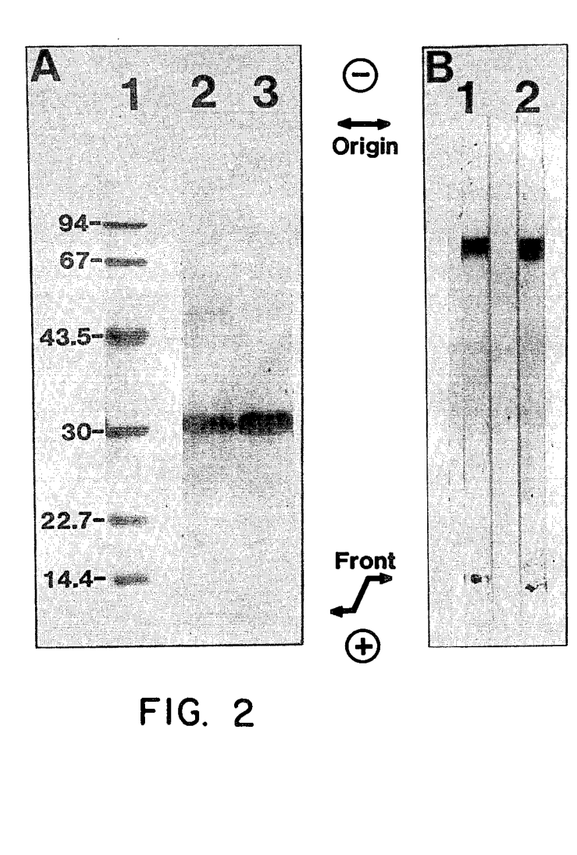
Figure 3:
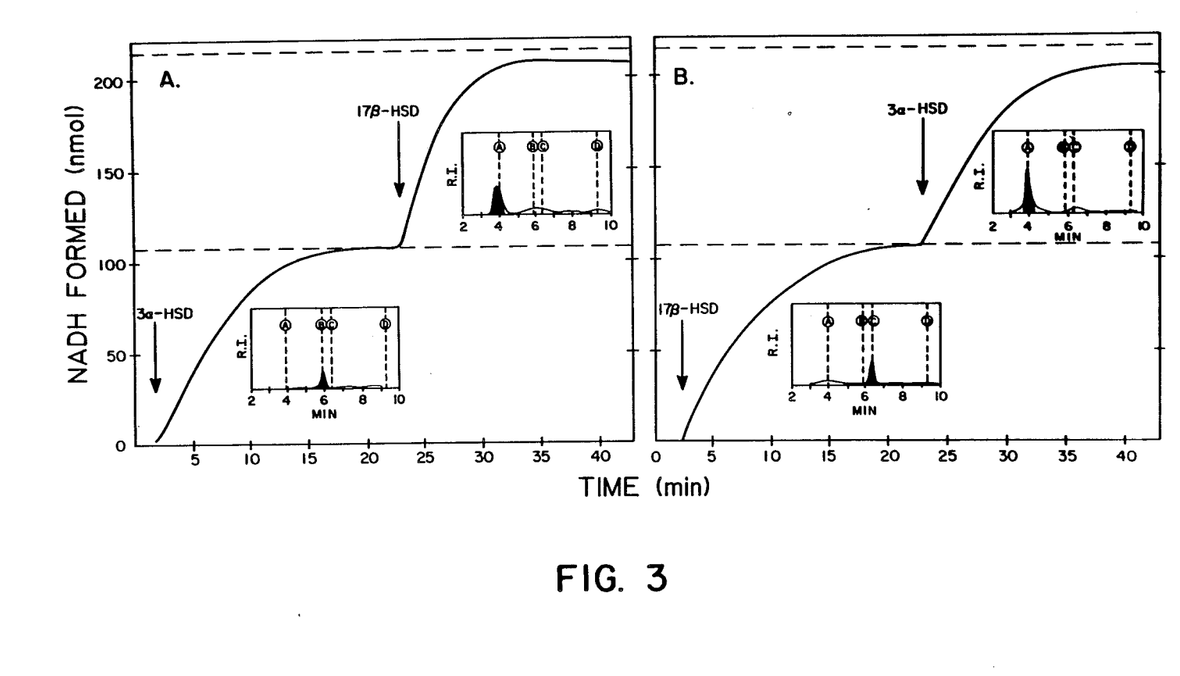

FIG. 3 demonstrates an example of just such a selective preparation of a steroid product from its precursor by 17β-HSD.

A further example of the preparative use of 17β-HSD in the enzymatic synthesis of a commercially unavailable radioactive steroid is now described.

34.5 nmol of [1,2-³H]-4-androstene-3,11,17-trione prepared by sodium bismuthate oxidative cleavage of commercially available [1,2-³H]-cortisone is incubated at 24° C. for 10 min in a 1 ml-system containing 3 mM NADH, 0.7 unit 17β-HSD of the present invention, and 50 mM potassium phosphate, pH 7. A 98.6% conversion (as

TABLE VIII

| | Differences Amoung Various Bacterial Hydroxysteroid Dehydrogenases | | | | | | |
|---|---|---|---|---|---|---|---|
| | Alcaligenes[1] | | P. Testosteroni | | P. Testosteroni TB | | B. Sterolicum[8] |
| Characteristics | 17β-HSD | 3β-HSD | 3(17)β-HSD | 3α-HSD | 3α-HSD | 3β-HSD | 3(17)β-HSD |
| Specificity for 17β-hydroxysteroids | Yes | No | Yes[2,3,4] | No[3] | No[4,7] | No[4,7] | Yes |
| Specificity for β-hydroxysteroids | No | Yes | Yes[2,3,4] | No[3] | No[4,7] | Yes[4,7] | Yes |
| Specificity for 3α-hydroxysteriods | No | No | No[3,4] | Yes[3] | Yes[4,7] | No[4,7] | No |
| Isoelectric point | 5.1 (1 species) | NA | 6.5–7.5[2,5] (multiple species) | 6.1[5] (multiple species) | NA | NA | NA |
| Subunit Molecular Weight (× 10⁻³) | 32 | NA | 23.5[2] | 25[6] | NA | NA | NA |
| Native Molecular Weight (× 10⁻³) | 68–86 | NA | 98–100[2,5] | 47[5] | NA | NA | NA |

NA means not available
[1]Payne & Talalay, J. Biol. Chem., November, 1985.
[2]Shultz et al., J. Biol. Chem., 252, 3775–3783, 1977.
[3]Talalay & Levy, Ciba Foundation Study Group, 2, 53–78, 1959.
[4]Roe & Kaplan, Biochemistry 8, 5093–5103, 1969.
[5]Squire et al., Biochem. Biophys. Acta., 89, 409, 1964.
[6]Skalhegg, Int. J. Peptide Protein Res., 7, 335–339, 1975.
[7]Shikita & Talalay, Analy. Biochem. 95, 286–292, 1979.
[8]Terada, et al. (1972) U.S. Pat. No. 3,776,816.

monitored by HPLC) to the product, [1,2-³H]-17β-hydroxy-4-androstene-3,11-dione, is thus achieved. It is emphasized that this product is not commercially available.

Figure 4:
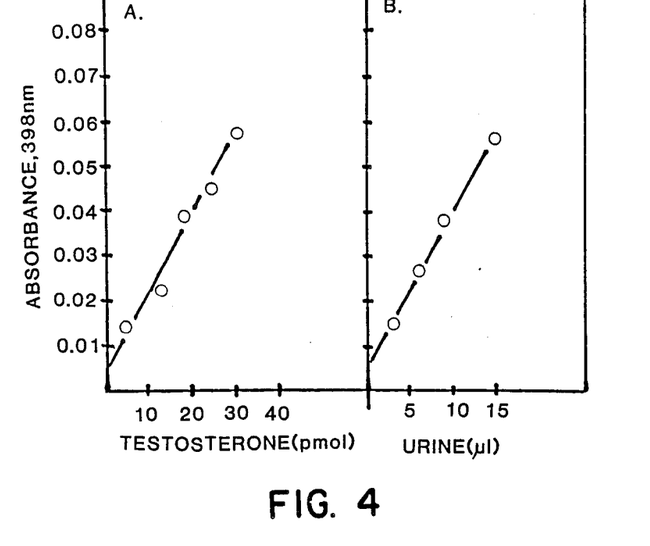
FIG. 4 shows a measurement of 17β-hydroxysteroids by transhydrogenase assay with 17β-HSD from Alcaligenes sp. The transhydrogenase assay was performed at pH 8.5 in a 0.6 ml system containing 0.2 mM NADH, 0.2 mM S-NAD and 0.024 unit of 17β-HSD. Incubation time was 6 h. Both samples were extracted with methanol following absorption to reverse phase chromatography medium (Sep Pak $C_{18}$, Waters Instr., Milford, MA). (A) Testosterone standard, 5 to 30 pmol (B) Hydrolyzed human male urine, 2.5 to 15 μl; this sample is calculated (from curve A) to contain 1.95 μM of total 17β-hydroxysteroids.

Analytical Applications of Hydroxysteroid Dehydrogenases (a) Microestimation of 17β-Hydroxysteroids and 17-Ketosteroids. The present invention is a one-step assay method for the measurement of minute quantities of 17β-hydroxy and/or 17-ketosteroids and is based on the novel application of the transhydrogenase function of the unique 17β-HSD of Alcaligenes. The invention is described in the following scheme, whereby the steroid-dependent transfer of hydrogen from NADH ($\lambda max = 340$ nm) to the thionicotinamide analog of NAD(S-NAD) is highly favorable at pH 8.5 and results in the production of S-NADH ($\lambda max = 398$ nm):

The invention described in this scheme is a one-step rate assay in which NAD, S-NAD, and 17β-HSD from Alcaligenes sp. are incubated with minute quantities of 17β-hydroxy- or 17- ketosteroids which catalyze the hydrogen transfer from NADH to S-NAD. S-NADH accumulates at a rate proportional to time, amount of enzyme, concentration of steroid, and the kinetic constants of the particular steroid for the enzyme (see FIG. 6). S-NADH is detected spectrophotometrically at 398 nm where NADH does not absorb. The high extinction coefficient of S-NADH ($11,300$ $M^{-1}$ $cm^{-11}$) favors high sensitivity. A linear response for the detection of steroids is achieved at room temperature (about 23°–28° C.), preferably at about 24° C. in systems of about 0.6 ml containing about: 70 mM Tris-HCl, pH 8.5; 0.2 mM NADH; 0.2 mM S-NAD and catalytic amount of 17β-HSD. For example, the rapid detection (2 h) of 10–150 pmol of testosterone is achieved using 74 ng (0.024 unit=μmol testosterone oxidized per min) 17β-HSD. Detection of less than 3 pmol of testosterone requires more time (about 12–16 hours) and 6 times as much enzyme. A convenient compromise assay allows the detection of 10–30 pmol of testosterone or of total 17β-hydroxy- and 17-ketosteroids in microliter quantities of hydrolyzed urine in only 6 hours with 74 ng (0.024 units) of 17β-HSD (FIG. 4A, B). Since the rate of S-NADH accumulation depends on several factors (supra), any of these factors may be adjusted to provide an assay of the desired sensitivity or working time. The low $K_m$ values of the 17β-HSD for steroid, NAD and NAD analog (Table VI) favor rapid cycling with relatively low concentrations of steroid.

Figure 5:
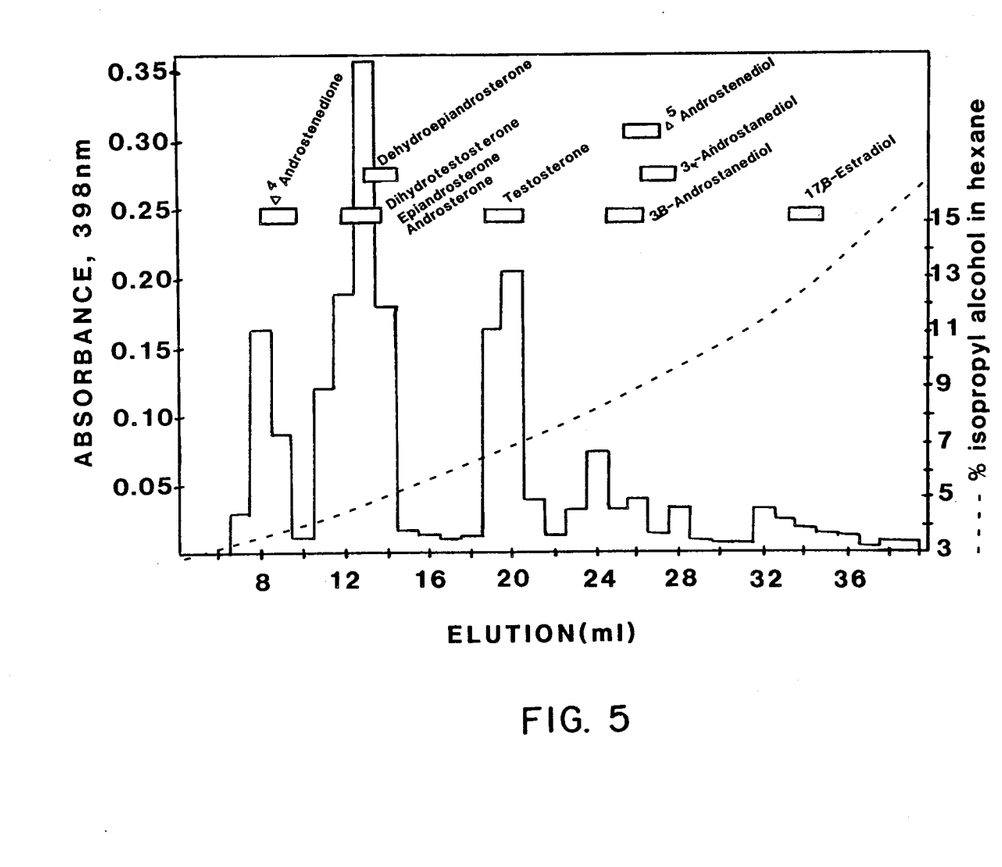
FIG. 5 shows measurement of individual 17β-hydroxy- and 17-ketosteroids in human male serum by transhydrogenase assay following separation on HPLC. An extract representing 235 μl of male serum was subjected to HPLC on a silica column containing functionalized diol groups (LiChrosorb Diol, EM Reagents, Gibbstown, NJ) and eluted at 2 ml/min with a concave gradient from 97:3 to 80:20 of hexane:isopropyl alcohol. The 1 ml fractions were dried and assayed by the transhydrogenase assay at pH 8.5 in a 0.6 ml system containing 0.2 mM NADH, 0.2 mM S-NAD, and 300 ng of 17β-HSD from Alcaligenes sp. Incubation time was 17 h. □ is the elution volume of standard steroids.
Figure 6:
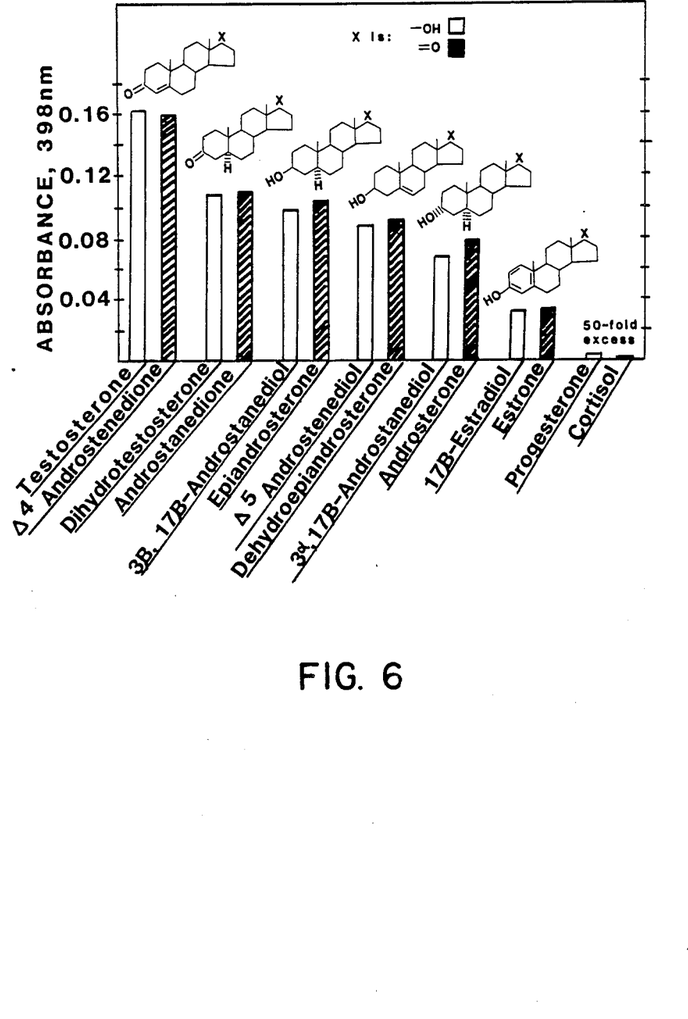
FIG. 6 shows the specificity of the transhydrogenase assay for 17β-hydroxy- and 17-ketosteroids. 50 pmol of each steroid except progesterone and cortisol (2500 pmol each) was assayed by the transhydrogenase assay using 148 ng of 17β-HSD and a 4 h incubation time.

Since 17β-HSD has specificity for all 17β-hydroxy and 17-ketosteroids (Table V), the transhydrogenase assay utilizing this enzyme provides a universal assay for these types of compounds (FIG. 6). The detection and measurement of individual steroids is then accomplished by routine chromatographic separation of the steroids. An example is shown in FIG. 5 which demonstrates the detection of individual steroids in human serum. The unique nature of this assay is emphasized in that unlike other steroid detection methods (i.e. radio-immunoassay) which can measure only one steroid at a time, the assay of the present invention simultaneously detects a "family" of steroids (i.e. those steroids with the biologically significant 17β-hydroxyl or 17-keto group), and thus is capable (following a separatory step) of providing a profile of steroids in a biological sample, and of detecting novel steroid metabolites. Of course, such an assay was not heretofore available.

Figure 7:
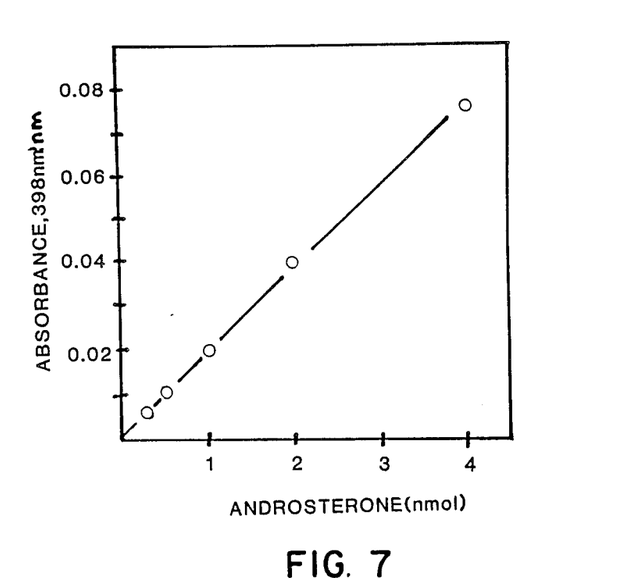
FIG. 7 shows the measurement of a 3α-hydroxysteroid (androsterone) by the transhydrogenase assay of the present invention but employing a hydroxysteroid dehydrogenase (3α-HSD from *Pseudomonas testosteroni* TB) not of the present invention. The transhydrogenase assay was performed at pH 8.5 in a 0.6 ml system containing 0.2 mM NADH, 0.2 mM S-NAD, 0.25 to 4 nmol of androsterone, and 0.05 unit of 3α-HSD from *P. testosteroni* TB. Incubation time was 3 h.

(b) Microestimation of other Hydroxy and Carbonyl Compounds. The above methods are clearly not confined to 17β-hydroxy- and 17-ketosteroids, but are applicable to other hydroxy- and ketosteroids or even non-steroidal compounds possessing hydroxyl or carbonyl groups which are enzymatically interconvertible. FIG. 7 demonstrates the detection of 3α-hydroxysteroid (androsterone) using the transhydrogenase assay of the invention but carried out with a 3α-HSD from Pseudomonas testosteroni. This particular 3α-HSD has specificity for bile acids as well as other steroids and can be employed to detect a variety of such compounds by means of the present invention. By analogy, any dehydrogenase, e.g. alcohol, glucose, sorbitol dehydrogenase and the like, can be used in an assay of the present invention to detect its appropriate hydroxyl and/or carbonyl substrate.

The present invention, of course, also makes it possible to provide the assay described herein in the form of a kit. A kit in accordance with the present invention comprises a single or a plurality of containers containing ingredients or mixtures thereof for performing the assay as fully described herein supra. Other components such as micropipettes, cuvettes, buffers, dyes with specific absorbance characteristics, instructions to carry out the assay and the like as ordinarily found in such kits are, of course, included in the kit if desired and necessary. The kit and the sensitive assay of the present invention allows convenient clinical as well as other usages and detection of steroids in human body or other biological samples, particularly of androgens in the sample which may be indicative of certain pathophysiological conditions related to disturbed steroid metabolism.

It is understood that having described the principles and illustrative examples for practising the present invention, such changes or modifications as immobilization of the enzymes, e.g. 17β-HSD on a solid support, and developing known types of immuno or enzyme linked immunoadsorbant assays and the like are well within the skill of the artisan in this field and all such modifications and embodiments are included as being suggested from the disclosure of the invention contained herein and are within the spirit, purview and scope of the appended claims.

We claim:

1. Biologically pure culture of a microorganism belonging to Alcaligenes genus deposited at ATCC under accession number 53265 and having the following properties:

(a) inducible to produce steroid transforming enzymes including 3β- and 17β-hydroxysteroid dehydrogenase and Δ$^5$-3-ketosteroid isomerase, said enzymes being separable and purifiable and effecting reversible oxido-reduction of 17β-hydroxyl and 17-ketone groups of $C_{18}$ and $C_{19}$ steroids containing a 17β-hydroxyl or 17-keto function, or 3β-hydroxyl and 3-ketone groups and of transformation of Δ$^5$-ketosteroids to Δ$^4$-ketosteroids.

2. Isolated, substantially pure 17β-hydroxysteroid dehydrogenase (17β-HSD) having the following properties: (a) molecular weight of about 32,000 when determined by sodium dodecyl sulphate polyacrylamide gel electrophoresis; (b) Km in μM range for steroids and nicotinamide nucleotides; (c) Vmax of greater than 300 μmol/min/mg protein for testosterone and estradiol-17β; (d) capable of stereospecific reversible oxidoreduction of the 17β-hydroxyl or 17-keto groups of $C_{19}$ androgenic and $C_{18}$ estrogenic steroids at about equal rates; and (e) substantially devoid of oxidoreductive activity at the 3-position of the steroid molecule.

3. An enzymatic assay for detecting hydroxyl or carbonyl compounds comprising reacting a hydroxyl or carbonyl compound or both in a buffered medium with an an NAD or NADP linked-dehydrogenase having specificity for reacting with said compound, transferring hydrogen from NADH or NADPH to an analog of NAD or NADP and measuring the rate of accumulation of the reduced analog of NAD or NADP.

4. The enzymatic assay of claim 3 wherein the dehydrogenase is a hydroxysteroid dehydrogenase.

5. The enzymatic assay of claim 4 employing isolated substantially pure 17β-hydroxysteriod dehydrogenase as the dehydrogenase.

6. The enzymatic assay of claim 5 wherein said compound is a 17β-hydroxy- or a 17-keto-steroid.

7. The enzymatic assay of claim 6 employing NADH and an analog of NAD which when reduced has an ultraviolet absorption maximum different from the ultraviolet absorption maximum of NADH.

8. The enzymatic assay of claim 7 wherein the analog of NAD is a thionicotinamide analog of NAD.

9. The enzymatic assay of claim 8 wherein the presence of 17β-hydroxy- and 17-ketosteroids are simultaneously detected.

10. The assay of claim 9 wherein the accumulation of reduced thionicotinamide analog of NAD is measured spectrophotometrically.

11. The assay of claim 10 wherein the reduced nicotinamide analog of NAD is measured at about 398 nm.

12. The assay of claim 3 wherein the buffered medium has a pH range of about 8 to 9.

13. The assay of claim 12 being performed at about 24° C. and the buffered medium is an aqueous buffered medium containing about 70 mM Tris-HCl, 0.2 mM NADH and 0.2 mM thionicotinamide analog of NAD at a pH of about 8.5.

14. The assay of claim 13 wherein the presence of 17β-hydroxy- and 17-ketosteroids in biological samples are detected.

15. A kit for detecting the presence of 17-hydroxy and 17-ketosteroids in biological samples comprising a container containing isolated, substantially pure 17β-hydroxysteroid dehydrogenase which is substantially free of 3β-hydroxysteroid dehydrogenase activity.

16. A method of detecting the profile of normal, abnormal, or artificially manipulated steroids in biological samples comprising quantitatively determining of the presence of all 17β-hydroxy- and 17-keto-steroids in the sample by the steps of (a) adding said sample to an aqueous reaction medium comprising about 70 mM Tris-HCl, 0.2 mM NADH and 0.2 mM S-NAD at a pH of about 8.5 and taking an initial reading at 398 nm; then (b) adding a catalytic amount of isolated, substantially pure 17β-hydroxysteroid dehydrogenase to the reaction medium; then (c) incubating the reaction medium in the dark at about 24° C. for sufficient time to accumulate measurable quantities of S-NADH; then (d) taking a final reading of the reaction medium at 398 nm; and then (e) calculating from a standard curve the amount of the steroid(s) from the difference between the final and the initial readings.

* * * * *